(12) United States Patent
Yoneda (10) Patent No.: US 11,185,272 B2
(45) Date of Patent: Nov. 30, 2021

(54) ELECTRODE EQUIPMENT

(71) Applicant: Panasonic Intellectual Property Management Co., Ltd., Osaka (JP)

(72) Inventor: Naotsugu Yoneda, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 1242 days.

(21) Appl. No.: 15/412,224

(22) Filed: Jan. 23, 2017

(65) Prior Publication Data

US 2017/0127968 A1 May 11, 2017

Related U.S. Application Data

(63) Continuation of application No. PCT/JP2016/000260, filed on Jan. 20, 2016.

(30) Foreign Application Priority Data

Jan. 26, 2015 (JP) .............................. JP2015-012072

(51) Int. Cl.
*A61B 5/00* (2006.01)
*A61B 5/282* (2021.01)
*A61B 5/11* (2006.01)
*A61B 5/349* (2021.01)

(52) U.S. Cl.
CPC ............ *A61B 5/282* (2021.01); *A61B 5/6804* (2013.01); *A61B 5/11* (2013.01); *A61B 5/349* (2021.01); *A61B 2560/0443* (2013.01); *A61B 2562/0219* (2013.01); *A61B 2562/125* (2013.01)

(58) Field of Classification Search
CPC .............. A61B 5/04085; A61B 5/6804; A61B 2560/0443; A61B 2562/0219; A61B 5/0425; A61B 5/11; A61B 2562/125; A61B 5/282; A61B 5/349; A61B 5/25; A61B 5/274; A61B 5/276

See application file for complete search history.

(56) References Cited

U.S. PATENT DOCUMENTS 4,317,457 A * 3/1982 Guillot ................. A61N 1/0408
607/115
2003/0088302 A1 5/2003 Shirakawa et al.
(Continued)

FOREIGN PATENT DOCUMENTS

JP 2000-070233 A 3/2000
JP 2001-245991 9/2001
(Continued)

OTHER PUBLICATIONS

International Search Report of PCT application No. PCT/JP2016/000260 dated Apr. 19, 2016.

*Primary Examiner* — Eun Hwa Kim
*Assistant Examiner* — Adam Z Minchella
(74) *Attorney, Agent, or Firm* — McDermott Will and Emery LLP (57) ABSTRACT

The electrode equipment of the present disclosure includes a first electrode, a second electrode having a different electrical polarity from the first electrode, and a sensor for detecting a vertical direction. The electrical polarities of the first electrode and the second electrode are determined based on output of the sensor.

4 Claims, 5 Drawing Sheets

(56) References Cited

U.S. PATENT DOCUMENTS

| | | | |
|---|---|---|---|
| 2005/0113703 A1* | 5/2005 | Farringdon | A61B 5/4812 |
| | | | 600/509 |
| 2007/0204706 A1 | 9/2007 | Kishimoto et al. | |
| 2008/0077027 A1* | 3/2008 | Allgeyer | A61B 5/25 |
| | | | 600/509 |
| 2009/0137883 A1 | 5/2009 | Chiba et al. | |
| 2011/0273548 A1 | 11/2011 | Uchiyama et al. | |
| 2012/0029309 A1* | 2/2012 | Paquet | A61B 5/6813 |
| | | | 600/301 |
| 2014/0296681 A1 | 10/2014 | Nakayama et al. | |
| 2015/0073231 A1* | 3/2015 | Beck | A61B 5/282 |
| | | | 600/301 |
| 2017/0185737 A1* | 6/2017 | Kovacs | A61B 5/02438 |

FOREIGN PATENT DOCUMENTS

| | | |
|---|---|---|
| JP | 2007-232575 | 9/2007 |
| JP | 2008-232903 A | 10/2008 |
| JP | 2009-131321 | 6/2009 |
| JP | 2012-511969 | 5/2012 |
| JP | 2014-190965 | 10/2014 |
| JP | 2014-200270 | 10/2014 |
| WO | 2010/075115 | 7/2010 |
| WO | 2010/143692 | 12/2010 |

* cited by examiner

ELECTRODE EQUIPMENT

BACKGROUND

Technical Field

The present disclosure relates to electrode equipment.

Description of the Related Art

Unexamined Japanese Patent Publication No. 2009-131321 discloses a capsule medical system having a plurality of electrodes serving as an electrode group for human body communication.

SUMMARY

According to the configuration disclosed in Unexamined Japanese Patent Publication No. 2009-131321, if equipment is attached in an incorrect direction, a polarity of an electrode may be mismatched, so that the equipment is likely to be operated incorrectly.

An objection of the present disclosure is to provide electrode equipment that is prevented from mismatching a polarity of an electrode irrespective of a direction in which the equipment is attached.

The electrode equipment of the present disclosure includes a first electrode, a second electrode having a different electrical polarity from the first electrode, and a sensor for detecting a vertical direction. The electrical polarities of the first electrode and the second electrode are determined based on output of the sensor.

Another electrode equipment of the present disclosure includes a first member on which a first electrode set is arranged, and a second member having a second electrode set that is arranged corresponding to arrangement of the first electrode set and a sensor for detecting a vertical direction. The first electrode set and the second electrode set are detachably attached to each other, and the electrical polarity of the second electrode set is determined based on output of the sensor.

The present disclosure can provide electrode equipment that prevents a polarity of an electrode from being reversed, irrespective of a direction in which the equipment is attached.

DETAILED DESCRIPTION

Hereinafter, exemplary embodiments will be described in detail with reference to drawings, if necessary. However, unnecessary detail description may be omitted. For instance, detail description of well-known matters or overlapped description of substantially the same configuration may be omitted. This is because the following description is avoided from being redundant unnecessarily and understood easily by those skilled in the art.

Note that, the applicant provides accompanying drawings and the following description in order for those skilled in the art to fully understand the present disclosure, but not intend to limit subject matter cited in claims.

Exemplary Embodiment

Hereinafter, as a practical exemplary embodiment of a system equipped with electrode equipment in accordance with the present disclosure, wear 100 of electrocardiographic detection system 10 and a configuration of biosensor device 200 will be described in detail. Electrocardiographic detection system 10 and biosensor device 200 each are an example of the electrode equipment.

Figure 1A:
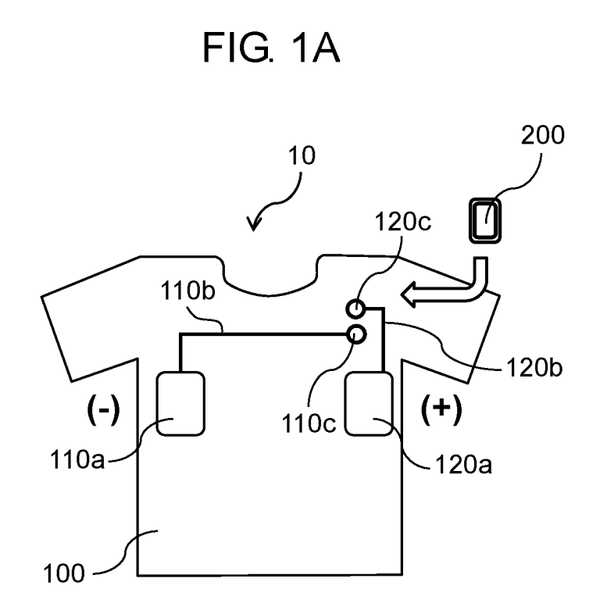
FIG. 1A is an image view in which a biosensor device is to be attached to electrodes on wear.
Figure 1B:
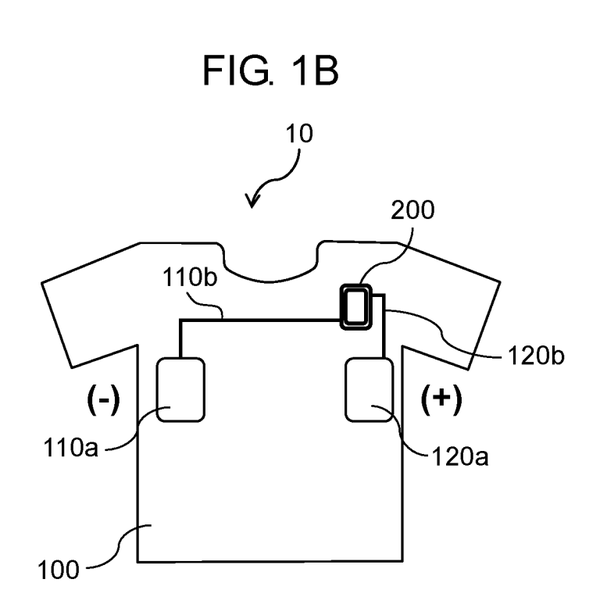
FIG. 1B is an image view in which the biosensor device is attached to the electrodes on the wear.
Figure 2:
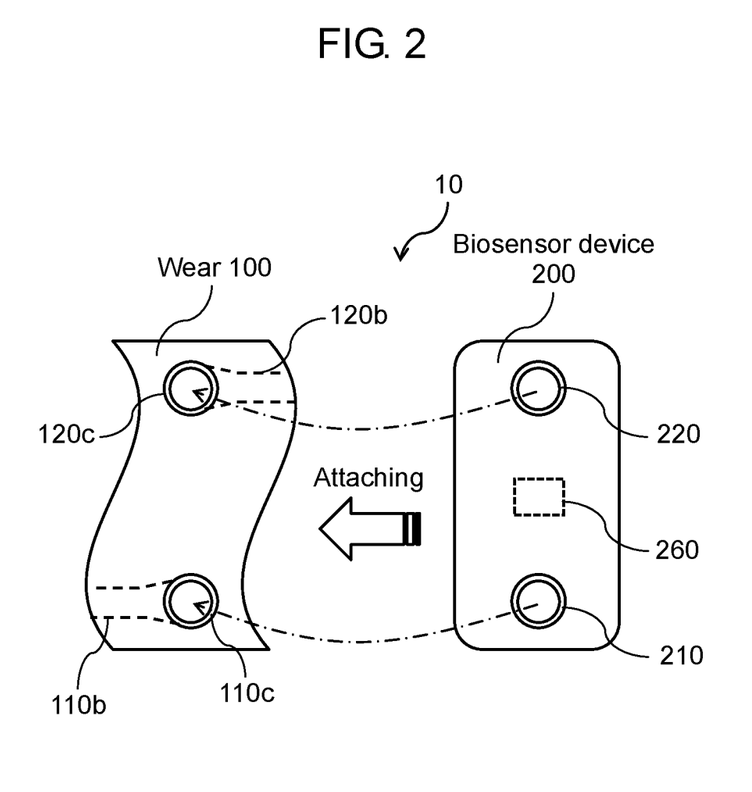
FIG. 2 is an image view expanding a state where the biosensor device is attached to the electrodes on the wear.

FIG. 1A and FIG. 1B show an example of wear 100 to be wore for detecting an electrocardiographic wave. FIG. 1A is an image view of wear 100 when biosensor device 200 is detached. FIG. 1B is an image view of wear 100 when biosensor device 200 is attached. Further, FIG. 2 is an image view expanding a state where biosensor device 200 is attached to electrodes on wear 100. To make it possible to wash wear 100, biosensor device 200 is configured to be detachably attached to wear 100 optionally.

First wear electrode 110 (110a, 110b, 110c) and second wear electrode 120 (120a, 120b, 120c) are formed in wear 100 as a pair of electrodes for detecting electrocardiography.

First wear electrode 110 is constituted by first contact part 110a to be in contact with human skin, first connecting portion 110c to be connected to biosensor device 200, and first wiring part 110b for connecting first contact part 110a and first connecting portion 110c electrically.

Likewise, second wear electrode 120 is constituted by second contact part 120a to be in contact with human skin, second connecting portion 120c to be connected to biosensor device 200, and second wiring part 120b for connecting second contact part 120a and second connecting portion 120c electrically.

First contact part 110a and second contact part 120a are formed into a pad-like shape by using, for example, a conductive fiber whose surface is coated with metal such as silver, carbon, and conductive organic matter. This makes it possible to secure comfortable contact with skin, while having conductivity. As shown in FIG. 1A and FIG. 1B, when a user puts on wear 100, first contact part 110a is disposed to be located on a right-hand side and second contact part 120a is disposed to be located on a left-hand side.

First wiring part 110b and second wiring part 120b are formed by using a conductive fiber as well as first contact part 110a and second contact part 120a are. Alternatively, if formed with a configuration that causes no uncomfortable contact with skin, they may be formed by using metal reed wires or the like.

As shown in FIG. 1A, first connecting portion 110c and second connecting portion 120c are disposed side by side in a vertical direction when a user puts on wear 100. In the example shown in FIG. 1A, first connecting portion 110c is disposed below second connecting portion 120c. To freely perform an electrical connection with biosensor device 200 serving as a detachable attachment partner, first connecting portion 110c and second connecting portion 120c are formed of a metallic button, a hook, and the like, or formed of a metallic material having magnetic attraction.

As shown in FIG. 2, biosensor device 200 includes first device electrode 210 and second device electrode 220. First device electrode 210 is connected to first connecting portion 110c of wear 100, and second device electrode 220 is connected to second connecting portion 120c of wear 100. The above connections each are performed mechanically and electrically with a removable configuration. Further, biosensor device 200 includes acceleration sensor 260. The acceleration sensor will be described later in detail.

Biosensor device 200 has such a function that electrocardiographic signals detected through first wear electrode 110 and second wear electrode 120 are arithmetically processed and communicated. Wear 100 and the biosensor device 200 are coupled to constitute electrocardiographic detection system 10 that detects electrocardiography derived from a heartbeat of a user wearing wear 100.

Herein, as shown in FIG. 1A and FIG. 1B, second wear electrode 120 has an electrical polarity of plus, and first wear electrode 110 has an electrical polarity of minus. Thus, if the electrical polarities of biosensor device 200, which is attached to wear 100, are mismatched with the electric polarities of first wear electrode 110 and second wear electrode 120, biosensor device 200 will fail to obtain correct electrocardiographic information.

On the other hand, a user is needed to check whether electrical polarities of the pair of electrodes are matched or not at every time when biosensor device 200 is attached to wear 100, thereby being troublesome to the user. Therefore, biosensor device 200 of the present disclosure includes acceleration sensor 260, and switches the electrical polarities of the electrodes to be connected to first wear electrode 110 and second wear electrode 120 according to output of acceleration sensor 260. This makes it possible to obtain correct electrocardiographic information constantly without a user being conscious of a direction in which biosensor device 200 is attached to wear 100.

Figure 3:
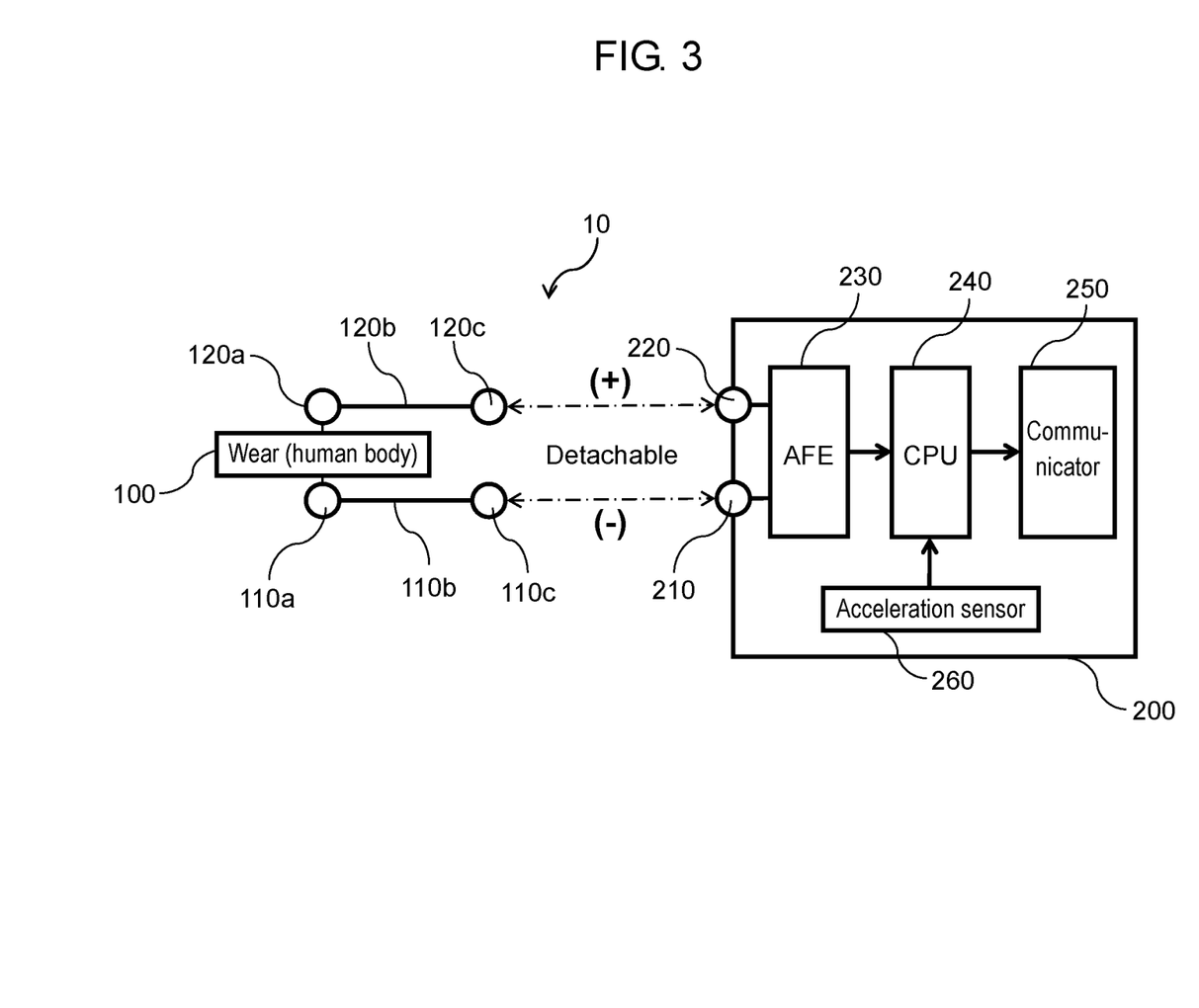
FIG. 3 is an electrical configuration diagram of electrodes on the wear and the biosensor device.

FIG. 3 is an electrical configuration diagram of biosensor device 200 and the electrodes on wear 100.

A circuit for processing an electrocardiographic signal electrically is built in biosensor device 200. That is, biosensor device 200 is constituted by first device electrode 210, second device electrode 220, AFE (Analog Front End) circuit 230 for performing analog signal processing, CPU 240 for performing digital arithmetic processing, communicator 250 for communicating data with other devices, acceleration sensor 260, a power source unit (not shown), and the like.

An electrocardiographic signal emitted from a human body is detected by first contact part 110a and second contact part 120a that are formed in wear 100 and in contact with a human body. The detected electrocardiographic signal is conveyed to first connecting portion 110c and second connecting portion 120c via first wiring part 110b and second wiring part 120b. Then, the electrocardiographic signal flows into AFE circuit 230 through first device electrode 210 and second device electrode 220 of biosensor device 200, which are connected to first connecting portion 110c and second connecting portion 120c.

AFE circuit 230 performs analog filtering, amplification processing, or the like with respect to the inputted electrocardiographic signal. Subsequently, AFE circuit 230 performs AD conversion of the electrocardiographic signal from an analog signal to a digital signal, and transmits the digitized electrocardiographic signal to CPU 240.

CPU 240 performs various kinds of digital arithmetic processing such as digital filtering and other processing with respect to the digitized electrocardiographic signal. After that, CPU 240 transmits the digitally processed electrocardiographic signal to communicator 250.

Communicator 250 is constituted by wireless communication means such as Bluetooth (registered trademark) and WiFi, or wire communication means such as USB. Communicator 250 transmits the digitally processed electrocardiographic signal to an external device having a display unit or the like. The external device, which has received the digitally processed electrocardiographic signal, draws an electrocardiographic wave and displays it on the display unit. Note that, communicator 250 may transmit the electrocardiographic signal to a device of a drawing part in real time, or may also transmit data of the electrocardiographic signal stored in a memory, if necessary.

Acceleration sensor 260 is disposed in biosensor device 200 such that a detectable axis of acceleration is directed along the vertical direction when a user puts on wear 100 and stands up straight in the state where biosensor device 200 is attached to wear 100 in a correct direction. Acceleration sensor 260 transmits the detected acceleration signal to CPU 240. Note that, acceleration sensor 260 may commonly be used as a sensor for achieving functions such as a pedometer (registered trademark) and an activity meter.

The power source unit (not shown) supplies a power source such that AFE circuit 230, CPU 240, and communicator 250 can be driven electrically. From viewpoints of noise reduction, portability, and the like, a battery is used as the power source unit in many cases, but a power source configuration such as an AC adapter may be employed.

Subsequently, an operation of biosensor device 200 configured as above will be described.

Figure 4:
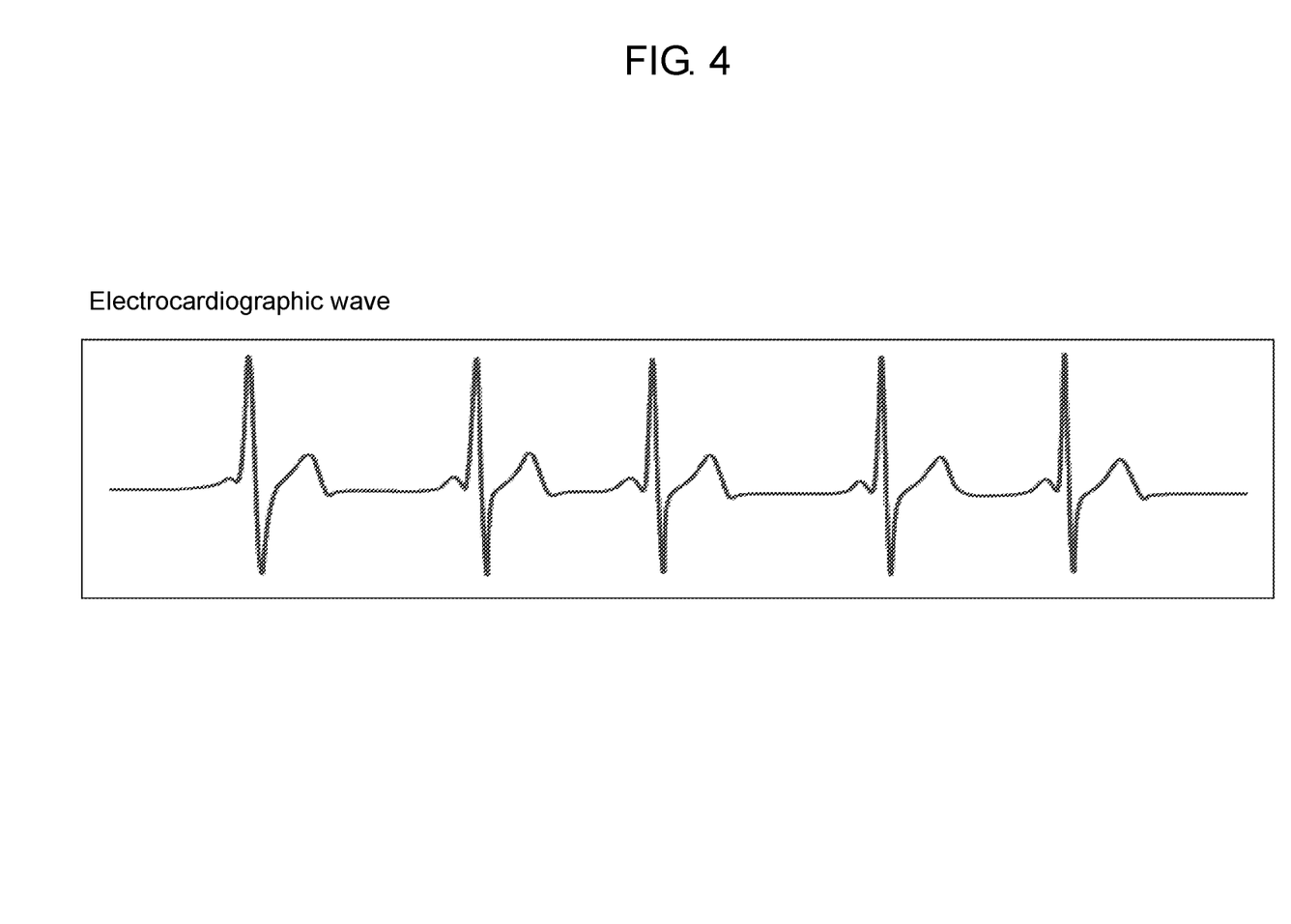
FIG. 4 is an image view of an electrocardiographic wave detected through the electrodes on the wear.

An electrocardiographic wave with a shape as shown in FIG. 4 has polarities of plus and minus. For that reason, if biosensor device 200 fails to detect an electrocardiographic signal with a correct polarity, a polarity of the electrocardiographic wave will be reversed. This is likely to cause a defect in electrical processing within the biosensor device 200, or to reverse the polarity of the electrocardiographic wave that is communicated and displayed on an external device disadvantageously.

Accordingly, in the present exemplary embodiment, CPU 240 determines whether or not biosensor device 200 is attached to wear 100 in a correct direction based on a polarity of a gravitational acceleration signal detected by acceleration sensor 260. Further, based on the above determination result, CPU 240 determines whether the electrocardiographic wave is processed as it is or processed after a polarity of the electrocardiographic wave is reversed.

Figure 5A:
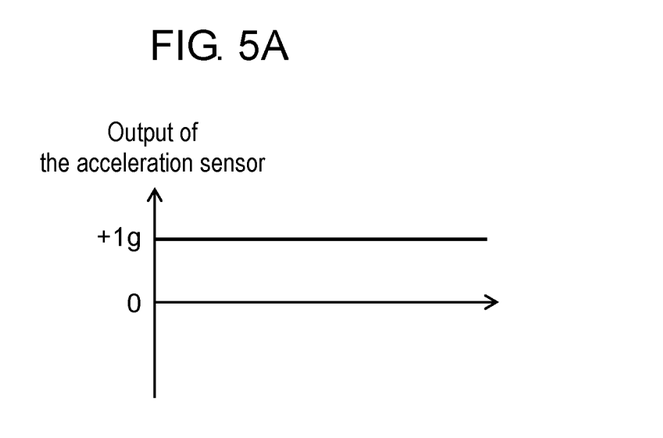
FIG. 5A is a view for explaining output (plus) of an acceleration sensor when the biosensor device is attached to the wear.
Figure 5B:
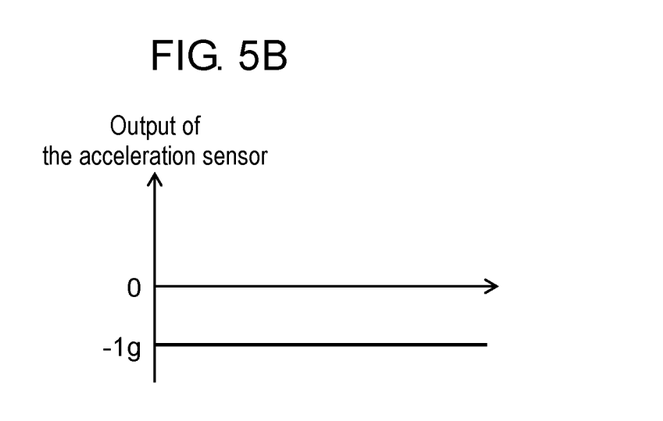
FIG. 5B is a view for explaining output (minus) of the acceleration sensor when the biosensor device is attached to the wear.

FIG. 5A is a view for explaining output of acceleration sensor 260 when biosensor device 200 is attached in a regular direction, and FIG. 5B is a view for explaining output of acceleration sensor 260 when biosensor device 200 is attached in a reverse direction. When a user attaches biosensor device 200 to wear 100 in the regular direction, acceleration sensor 260 transmits an acceleration signal indicating an acceleration value equivalent to a gravity of +1 g to CPU 240, as shown in FIG. 5A. On the other hand, when a user attaches biosensor device 200 to wear 100 in a direction reverse to the regular direction, acceleration sensor 260 transmits an acceleration signal indicating an acceleration value equivalent to a gravity of −1 g to CPU 240, as shown in FIG. 5B.

When the acceleration signal indicating a gravity of +1 g is inputted, CPU 240 determines that biosensor device 200 has been attached in the regular direction, and then processes the electrocardiographic wave as it is. On the other hand, when the acceleration signal indicating a gravity of −1 g is inputted, CPU 240 determines that biosensor device 200 has been attached in the reverse direction, and then processes the electrocardiographic wave after positive and negative polarities thereof are reversed.

That is, even if biosensor device 200 is connected to wear 100 in either of the above directions, CPU 240 can process an electrocardiographic wave based on a correct polarity of the electrocardiographic wave. Thus, a user can eliminate such troublesomeness that a direction of biosensor device 200 is necessary to be checked at the time when biosensor device 200 is attached to wear 100.

The timing when CPU 240 determines polarities of first device electrode 210 and second device electrode 220 based on the signal from acceleration sensor 260 may be synchronized with timing when an electrocardiographic signal is detected, or may be synchronized with timing when a power source of biosensor device 200 is turned on.

Other Exemplary Embodiments

As above, the exemplary embodiment is described as an exemplary art disclosed in this application. However, the art in the present disclosure is not limited to this, but can also be suitably applied to an exemplary embodiment in which modifications, replacement, addition, omission, and the like are made if necessary. Further, the respective components described in the above exemplary embodiment may be combined to configure a new exemplary embodiment. Hereafter, other exemplary embodiments will be described.

In the above exemplary embodiment, a form of shirt is shown as wear 100, but the present disclosure is not limited to this. That is, other forms such as pants, tights, and socks, other than a shirt, may be used as wear 100.

In the above exemplary embodiment, biosensor device 200, which processes an electrocardiographic wave, is exemplified as electrode equipment, but the present disclosure is not limited to this. That is, the electrode equipment of the present disclosure may be applied to any devices other than biosensor device 200, if the devices are detachable. In other words, the electrode equipment may be applied to a device equipped with a pair of electrodes that are arranged side by side in a vertical direction and have polarities.

In the above exemplary embodiment, when a user puts on wear 100, first connecting portion 110*c* is arranged below second connecting portion 120*c* as shown in FIG. 1A, but the upper and lower sides may also be arranged reversely. In this case, a relationship between first device electrode 210 and second device electrode 220 of biosensor device 200 is also reversed.

In the above exemplary embodiment, wear 100 has first wear electrode 110 and second wear electrode 120 as a pair of electrodes, and biosensor device 200 includes first device electrode 210 and second device electrode 220 as a pair of electrodes, but not limited to these. The first wear electrode, the second wear electrode, the first device electrode and the second device electrode may be respectively divided into two or more electrodes. And a wear may have three or more wear electrodes as an electrode set, and a biosensor device may include three or more device electrodes as an electrode set.

In the above exemplary embodiment, acceleration sensor 260 is used for determining which direction the pair of electrodes in the electrode equipment is directed in a vertical direction, but not limited to this. For instance, an actuator that is displaced according to the direction in a vertical direction, or the like is provided and the displacement of the actuator may be detected by a photosensor or the like to determine a mounting direction of the electrode equipment.

As above, the exemplary embodiment is described to exemplify the art in the present disclosure. To achieve the purpose, the accompanying drawings and detailed description are provided.

Accordingly, in the structural elements described in the accompanying drawings and detailed description, not only a structural element essential to solve the problem but also a structural element non-essential to solve the problem may be included to exemplify the above art. Therefore, the non-essential structural element should not be interpreted to be essential promptly, even if being described in the accompanying drawings and detailed description.

Further, the above exemplary embodiment is provided to exemplify the art in the present disclosure. Therefore, various modifications, replacement, addition, omission, and the like may be made within a scope of claims or its equivalent range.

The electrode equipment in the present disclosure is not limited to application to a biosensor device, but can be applied to various kinds of devices necessary to be detachable.

What is claimed is:

1. An electrocardiographic detection system comprising:
a sensor device that is removably attached to an electrode set of a garment, the sensor device including:
a housing having a surface adapted to connect to the electrode set of the garment;
a first electrode connecting member disposed on the surface of the housing; and
a second electrode connecting member disposed on the surface of the housing spaced apart from the first electrode connecting member and having a different electrical polarity from the first electrode connecting member;
an acceleration sensor that is located within the housing between the first electrode connecting member and the second electrode connecting member, the acceleration sensor being configured to output an acceleration value; and
a processor disposed within the housing and operatively coupled to the first and second electrode connecting members and the acceleration sensor and configured to:
receive a signal sensed by the acceleration sensor and determine whether or not the acceleration value is less than zero based upon the signal sensed by the acceleration sensor,
determine whether or not the sensor device is attached to the electrode set of the garment in a reverse direction based upon the acceleration value, and
reverse, in response to the determination that the sensor device is attached to the electrode set of the garment in the reverse direction, electrical polarities of the first electrode connecting member and the second electrode connecting member.

2. The electrode equipment according to claim 1, wherein the electrode set of the garment comprises a first biosensor electrode and a second biosensor electrode.

3. An electrocardiographic detection system comprising:
a first member having an electrode set; and
a sensor device comprising:
a housing having a surface adapted to connect to the electrode set of the first member;

a first electrode connecting member disposed on the surface of the housing and a second electrode connecting member disposed on the surface of the housing spaced apart from the first electrode connecting member, wherein the first electrode connecting member and the second electrode connecting member are arranged corresponding to an arrangement of the electrode set;

an acceleration sensor that is located within the housing between the first electrode connecting member and the second electrode connecting member, the acceleration sensor being configured to output an acceleration value, and a processor disposed within the housing and operatively coupled to the first and second electrode connecting members and the acceleration sensor;

wherein the electrode set of the first member includes a first connecting portion and a second connecting portion respectively corresponding to the first electrode connecting member and the second electrode connecting member of the sensor device, the first connecting portion and the second connecting portion of the first member are disposed in a vertical direction with respect to one another on the first member, the electrode set of the first member and the sensor device are detachably attached to each other, and the processor is configured to:

receive a signal sensed by the acceleration sensor and determine whether or not the acceleration value is less than zero based upon the signal sensed by the acceleration sensor, determine whether or not the sensor device is attached to the electrode set in a reverse direction based upon the acceleration value, and reverse, in response to the determination that the sensor device is attached to the electrode set in the reverse direction, an electrical polarity of the first electrode connecting member and the second electrode connecting member.

4. The electrode equipment according to claim 3, wherein the electrode set of the first member further comprises a first biosensor electrode and a second biosensor electrode.

* * * * *